US00RE38712E

(19) United States
(12) Reissued Patent
Wyborny et al.

(10) Patent Number: US RE38,712 E
(45) Date of Reissued Patent: Mar. 22, 2005

(54) METHOD AND APPARATUS FOR STORING SIGNALS IN AN IMPLANTABLE MEDICAL DEVICE

(75) Inventors: Paul Wyborny, Lake Oswego, OR (US); Indra Nigam, Lake Oswego, OR (US); Max Schaldach, Erlangen (DE)

(73) Assignee: Biotronik Mess- und Therapiegeraete GmbH & Co., Berlin (DE)

(21) Appl. No.: 10/294,745

(22) Filed: Nov. 15, 2002

Related U.S. Patent Documents

Reissue of:
(64) Patent No.: 5,836,889
Issued: Nov. 17, 1998
Appl. No.: 08/806,754
Filed: Mar. 3, 1997

(30) Foreign Application Priority Data

Mar. 4, 1996 (DE) ..... 196 09 411

(51) Int. Cl.[7] ..... A61B 5/04; G01D 1/12
(52) U.S. Cl. ..... 600/509; 600/515; 607/9
(58) Field of Search ..... 607/9; 600/508, 600/509, 515, 517, 518

(56) References Cited

U.S. PATENT DOCUMENTS 4,716,903 A * 1/1988 Hansen et al. ..... 607/9
4,920,489 A * 4/1990 Hubelbank et al. ..... 607/9
5,301,677 A * 4/1994 Hsung ..... 600/518
5,312,446 A * 5/1994 Holschbach et al. ..... 607/9
5,404,877 A * 4/1995 Nolan et al. ..... 600/484

FOREIGN PATENT DOCUMENTS

EP 0149094 * 7/1985
EP 0263599 * 4/1988
EP 0512667 * 11/1992

OTHER PUBLICATIONS

S.M. Blanchard et al.: "Comparison of methods for adaptive sampling of cardia electrograms and electrocardiograms". In: Medical & Biological Engineering & Computing: Jul. 1985; pp. 377–386.*

* cited by examiner

*Primary Examiner*—Carl Layno
(74) *Attorney, Agent, or Firm*—Venable LLP; Catherine M. Voorhees

(57) ABSTRACT

A method of storing signals having a course over time in an implantable medical device, and/or transmitting the signals out of the device and out of the patient's body, with the course over time being detected in the device, particularly at predetermined time intervals with a constant sampling interval, and a sequence of signal samples being obtained therefrom, of which a partial quantity is stored and/or transmitted as the result of a selection made with a predetermined selection criterion, with the selection criterion being the first derivation of the course over time of the signals according to time, and with the selection being made such that the first derivation of the straight-line connection between an nth and the (n−1)th signal sample is determined and compared to the first derivation of the straight-line connection between the [(n−1)th] *nth* signal sample and the last-stored and/or last-transmitted signal sample, and the [nth] *(n−1)th* signal sample is then stored and/or transmitted as the new last signal sample exactly when these first derivations differ by more than a predetermined value.

15 Claims, 7 Drawing Sheets

| $L_2$ | $L_1$ | $L_0$ | S | $V_3$ | $V_2$ | $V_1$ | $V_0$ | segment length | end pt. op. sign | end pt. value |
|---|---|---|---|---|---|---|---|---|---|---|
| $L_2$ | $L_1$ | $L_0$ | X | X | X | X | X | $(L_2{:}L_0)$ $(0 \Rightarrow 8)$ | n/a | n/a |
| X | X | X | 0 | X | X | X | X | n/a | - | n/a |
| X | X | X | 1 | X | X | X | X | n/a | + | n/a |
| X | X | X | X | 0 | $V_2$ | $V_1$ | $V_0$ | n/a | n/a | $(V_3{:}V_0)*V_{max}/32$ |
| X | X | X | X | 1 | $V_2$ | $V_1$ | 0 | n/a | n/a | $(V_3{:}V_0)*V_{max}/32$ |
| X | X | X | X | 1 | $V_2$ | $V_1$ | 1 | n/a | n/a | $2*((V_3{:}V_0)-1)*V_{max}/32$ |

Fig.3

| S | V | S | V | S | V | S | V |
|---|---|---|---|---|---|---|---|
| 0 | 0 | 8 | 8 | 16 | 9 | 24 | 13 |
| 1 | 1 | 9 | 8 | 17 | 9 | 25 | 13 |
| 2 | 2 | 10 | 10 | 18 | 9 | 26 | 13 |
| 3 | 3 | 11 | 10 | 19 | 9 | 27 | 13 |
| 4 | 4 | 12 | 12 | 20 | 11 | 28 | 15 |
| 5 | 5 | 13 | 12 | 21 | 11 | 29 | 15 |
| 6 | 6 | 14 | 14 | 22 | 11 | 30 | 15 |
| 7 | 7 | 15 | 14 | 23 | 11 | 31 | 15 |

Fig.4

| status | clock | P CLR | P CLK | S CLR | S CLK | E CLR | E CLK | N CLR | N CLK | ALU CLRA | ALU CLRB | ALU CLRZ | ALU SEL (1)T | ALU ASEL (0)T | ALU ASEL (1)T | ALU BSEL (0)T | ALU S_A | ALU CLK | T CLR | T CLK | VRTX |
|---|---|---|---|---|---|---|---|---|---|---|---|---|---|---|---|---|---|---|---|---|---|
| 0 | 0 | active only with total reset 0 | 1 | active only with total reset 0 | 0 | active only with total reset 0 | 0 | 0 | 0 | 1 | 1 | 1 | 0 | 0 | 0 | 0 | 1 | 0 | 1 | 0 | 0 |
| 1 | 0 | | 1 | | 0 | | 0 | 0 | 0 | 0 | 0 | 0 | 0 | 0 | 0 | 0 | 1 | 0 | 0 | 0 | 0 |
| | 1 | | 0 | | 1 | | 0 | 1 | 1 | 0 | 0 | 0 | 0 | 0 | 0 | 0 | 1 | 0 | 0 | 0 | 0 |
| 2 | 0 | | 1 | | 0 | | 0 | 0 | 0 | 1 | 0 | 0 | 0 | 1 | 0 | 1 | 1 | 0 | 0 | 0 | 0 |
| | 1 | | 0 | | 0 | | 0 | 0 | 0 | 0 | 0 | 0 | 0 | 0 | 0 | 0 | 1 | 0 | 0 | 0 | 0 |
| 3 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 4 | 0 | | 1 | | 0 | | 0 | 0 | 0 | 0 | 0 | 0 | 0 | 1 | 1 | 1 | 1 | 0 | 0 | 0 | ? |
| | 1 | | 0 | | 0 | | 0 | 0 | 0 | 0 | 0 | 0 | ?(0) | 0 | 0 | 0 | 1 | 0 | 0 | 0 | ? |
| 5 | 0 | | 1 | | 0 | | 0 | 0 | 0 | 0 | 0 | 0 | 0 | 1 | 1 | 1 | 1 | 0 | 0 | 0 | ? |
| | 1 | | 0 | | 0 | | 0 | 0 | 0 | 0 | 0 | 0 | ?(1) | 0 | 0 | 0 | 1 | 0 | 0 | ?(1) | ? |
| 6 | 0 | | 1 | | 0 | | 0 | 0 | 0 | 0 | 0 | 0 | 0 | 1 | 1 | 1 | 1 | 0 | 0 | 0 | ? |
| | 1 | | 0 | | 0 | | 0 | 0 | 0 | 0 | 0 | 0 | ?(2) | 0 | 0 | 0 | 1 | 0 | 0 | ?(2) | ? |
| 7 | 0 | | 1 | | 0 | | 0 | 0 | 0 | 0 | 0 | 0 | 0 | 1 | 1 | 1 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | ?(3) | ? |
| 8 | 0 | | 1 | | 0 | | 0 | 0 | 0 | 1 | 0 | 0 | 1 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 9 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ?(5) |
| 10 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 11 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 12 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 13 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 14 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | 0 | 0 | 0 | 0 | 0 | 0 | 0 | 0 | 1 | 0 | 0 | 0 | ? |
| 15 | 0 | | 1 | | 0 | | 0 | 0 | 0 | 0 | 0 | 0 | 0 | 0 | 0 | 0 | 1 | 0 | 0 | 0 | ? |
| | 1 | | 0 | | 0 | | 0 | 0 | ?(6) | 0 | 0 | 0 | 0 | 0 | 0 | 0 | 1 | 0 | 0 | 0 | ? |

Fig.7

METHOD AND APPARATUS FOR STORING SIGNALS IN AN IMPLANTABLE MEDICAL DEVICE

Matter enclosed in heavy brackets [ ] appears in the original patent but forms no part of this reissue specification; matter printed in italics indicates the additions made by reissue.

BACKGROUND OF THE INVENTION

The invention relates to a method of storing signals having a course over time in an implantable medical device, and/or transmitting the signals out of the device and out of the patient's body, with the course over time being detected in the device, particularly at predetermined time intervals with a constant sampling interval, and a quantity of signal samples being obtained therefrom, of which a partial quantity is stored and/or transmitted as the result of a selection made with a predetermined selection criterion, and an apparatus for executing the method.

The detection and evaluation of physiologically-relevant signals in the body with suitable detection or monitoring devices are in step with the continuously-expanding use of implantable medical devices such as cardiac pacemakers or defibrillators. The operation of the implantable device is controlled on the basis of the results of, for example, the detection and evaluation of the course over time of cardiac-action potentials or the interior cardiac pressure or volumetric impedance measurements, etc. In addition to, or independently of, the first-mentioned function, the data can be used for a separate medical diagnosis and/or analysis of the operating state of the device itself.

The relevant signals typically result in analog form as high-resolution measurement curves, and, for many applications, must be registered over a relatively lengthy time period and kept ready for a comparative evaluation. In conventional handling, this requires storage of a large quantity of data in the implantable device and/or transmission of the data to the outside, and, finally, appropriate data processing. The rapid advances in the production of cost-effective semiconductor memories having very large storage capacities, and in processor technology, have significantly increased the relevant possibilities in implantable devices; nevertheless, it is desirable to limit the quantity of data in order to reduce costs and effect the lowest-current operation possible. This applies particularly to devices in which it is desirable to detect and handle numerous types of relevant data over periods of days and weeks, for example for automatic pacemaker/cardioverters.

One possibility known from a plurality of technical applications—particularly communication and measuring techniques—is data compression. Numerous data compression methods are described in detail in the relevant literature.

These techniques have not yet been able to gain a foothold in the field of storage and transmission of physiological data, particularly in implantable devices, partly because of the high cost of the device technology and partly because of the specifics of the signals occurring here and the information to be obtained over the course of the signal processing. Thus, as before, in this field the resulting data are typically stored in digitized form, without compression.

This is the path followed by an EKG monitor according to EP 0 512 667 A1, which uses a diskette or similar data carrier as a storage medium.

EP 0 149 094 B1 describes a non-implantable recording system for the time-compromised registration of EKG wave forms. The key factor of this system is simply the reduction of the resolution capability of a conventional registration to recording paper, which is effected here by a thermo-line printer. The system only serves in a first screening as the precursor of the later, more precise detection of arrhythmia states, and is not suited for obtaining precise diagnostic information, and is especially ill-suited for controlling implanted devices.

An EKG data compression for storing EKG data in a pacemaker memory is described in EP 0 263 599 A2. This compression is based on the condition that the EKG signal is constant (lies near the zero line) for the majority of a cardiac cycle, so no signal value needs to be stored for these times. Therefore, the time span between predetermined changes in the EKG signal is stored, so the method represents a time-related variation of the known delta modulation. Turning points in the signal course are characterized by additional storage of a flag.

If this method is intended to effect a resolution that permits the reliable, autonomous control of a combination anti-arrhythmia device, a large amount of storage space is required for storing the precise times at which the signal changes occur, and the time-data conditioning for the actual (particularly comparative) evaluation requires a substantial outlay.

U.S. Pat. No. 5,312,446 describes an implantable medical device having a telemetry device that includes a storage of detected physiological signals with—selectively, multiple-stage—data compression. The compression process is based on step-wise separation of a few significant measuring points based on a comparison of the absolute measured values at consecutive sampling points. The (compromised) data are stored in analog form, which requires the provision of a special memory.

SUMMARY OF THE INVENTION

It is an object of the invention to disclose a method of the generic type described at the outset, and an apparatus for executing the method, that permit processing of the (physiological) signals detected with an implantable medical device for reliably controlling the device, and/or for diagnostic purposes, with a comparatively low storage and processing outlay and current consumption.

This object is accomplished by a method having steps of sensing physiological signal of a patient's body, selecting sections of the sensed physiological signal and storing the selected sections of sensed physiological signals wherein the selection criteria is the first derivation of the course over time of the signals according to time, with the selecting step being made such that the first derivation of the straight-line connection between an nth and the (n−1)th signal sample is determined and compared to the first derivation of the straight-line connection between the [(n−1)th] *nth* signal sample and the last-stored signal sample and the storing step stores the [nth] *(n−1)th* signal sample as the new last signal sample exactly when these first derivations differ by more than a predetermined value.

Likewise, the object is achieved by[; change "the features of" to] a timer for establishing sampling intervals, a signal recorder for recording the signal-amplitude value in the sampling intervals, a processing unit that is connected to the timer and at least indirectly to the signal recorder for processing the recorded signal-amplitude values corresponding to a predetermined algorithm, and for outputting a memory-control signal as a result of the processing, a counter that is connected to the output of the timer and, by way of a reset input, to the control-signal output of the processing unit for counting the sampling intervals in response to the memory-control signal, and for outputting an interval-counter value that is also supplied to the processing unit, a memory that can be at least indirectly connected to the output of the signal recorder and the output of the counter for storing signal samples from the counter status, signal operational sign and signal amplitude as data words, and a memory-control unit that is connected to the control-signal output of the processing unit for producing a connection between the output of the signal recorder and the output of the counter and the memory in response to the memory-control signal, and for effecting storage of the current signal sample, with the processing unit having: a first and second intermediate-storage unit for intermediate storage of the signal sample that was last stored in the memory, and the second-to-last-recorded signal sample, an arithmetic stage that is at least indirectly connected to the outputs of the signal recorder and the counter, and the first and second intermediate-storage units, for calculating the first derivations of the straight-line connection between the current and second-to-last signal samples and the straight-line connection between the [second-to-last-] *current* and the last-stored signal samples, a subtraction stage that is connected to the arithmetic stage for forming the difference from the first derivations, a threshold-value memory for storing a difference threshold value, and a comparator unit that is connected on the input side to the subtraction stage and the threshold-value memory for comparing the difference of the first derivations to the difference threshold value, and for outputting the memory-control signal as a result of the comparison.

The invention encompasses the concept of selecting those sections of a physiological signal (or one generally characterized by its course over time) for storage or transmission in which the course changes significantly over time, while avoiding a storage or transmission of signal sections in which no significant change occurs.

Based on the stored signal samples, the course in the last sections can be approximated with their temporal reference point, with a sufficiently precise reconstruction of the entire signal being made possible with a lower storage or transmission capacity. This saving of capacity can be considerable, especially in signals of the EKG type, in which long sections having only slight changes in amplitude and short sections in which rapid changes significant for evaluation exist adjacently.

The disclosed method and the apparatus for executing it are equally suited for compression of current signals or signals recorded in or on the body of a patient, such as model or comparison data stemming from other sources, that are required in the medical device for its control or for diagnostic purposes. Of particularly practical interest is the application in the storage or transmission of short- and long-time EKGs or histograms for cardiac activity, especially of data or corresponding model data recorded within the scope of daily profiles or stress cycles or during occurrences of tachycardia.

In these connections, the method permits a considerable increase in the control intelligence of implanted pacemakers, defibrillators, cardioverters or medication-dosing devices, based on significantly-expanded possibilities, to a true signal-form processing in addition to standard processing of singular, logical or scalar measurement and comparison variables.

In an advantageous embodiment of the method, for every stored and/or transmitted signal sample, the operational sign, the amplitude value and the numerical value of the sampling interval that has passed since the last storage of a signal sample is stored or transmitted in a data word. The word width is oriented according to the processing width of the hardware configuration used.

The method permits a time-near transmission of the detected and compromised data without costly buffer storage of comprehensive data sets. Because the method requires a reference to the last signal sample that was accessed as being worth storing or transmitting, in the case of time-near transmission at least the last-transmittal signal sample is to be held in internal intermediate storage.

The signals compromised because of the method of the invention can primarily be cardiac-action signals, particularly an intracardially-recorded EKG or model or comparison signals transmitted from outside of the patient's body that represent cardiac-action signals. However, other time-dependent, physiological signals or comparison signals can also be used.

The method can be implemented particularly simply and cost-effectively with the hardware used in modern defibrillators and pacemakers if the sampling is connected to a digitization of the amplitude values; it is particularly advantageous for adequate storage and further evaluation, especially of cardiac signals, if the digitizing of smaller amplitude values is effected with higher resolution than that of large amplitude values.

The signal recorder is at least one—usually intracadially-, but also epicardially-disposed—electrode having a downstream sensing amplifier for detecting cardiac-action potentials.

In the apparatus for executing the method, the memory for the compromised signals is configured particularly as a semiconductor direct-access memory (RAM), and has a plurality of separately-accessible memory regions for respectively storing a signal-sample partial sequence, i.e., a compromised total signal. This permits the signals recorded at different times to be compared directly to one another and/or to comparison signals.

In the configuration that provides a transmission to the outside, the transmitting unit is configured as a telemetry transmitting unit (known per se).

In a manner that is advantageous for the majority of practical applications, both an internal memory and a transmitting unit can be provided, in which instance the transmitting unit can be connected to the memory for transmitting memory contents out of the device, and (internal or external) control means can also be provided that activate the transmitting unit on demand or at predetermined time intervals. This permits, for example, the autonomic, time-near activation of a defibrillator or cardioverter in (virtually immediate) response to the detection of signal forms which, when compared to signals or model signals that were recorded earlier, indicate a need for therapy. Furthermore, diagnostically-useful primary and secondary data (signal form comparison data) are thus made accessible to the physician for a more precise interpretation.

An extensively internal evaluation of the signal forms stored compromised, up to results of direct diagnostic usefulness, is advantageously possible if a calculation unit is provided for control or diagnosis data, the unit being connected on the input side to the memory for the signal-sample partial sequences and on the output side to, selectively, a control or diagnosis data memory, and configured for comparative processing of different stored signal samples for obtaining control signals or diagnostically-relevant data.

The integration of the apparatus into an implantable anti-arrhythmia device for treating arrhythmia of the heart, particularly a defibrillator and/or pacemaker—described above—or a medication-dosing device is of particular practical significance; components or assemblies of these devices can also be used to implement the method.

In an anti-arrhythmia device of this type, an operation-control unit is provided that is connected on the input side to the output of the above-mentioned control-data calculating unit and/or the control-data memory, the operation-control unit being configured to control the operation of the device based on the result of the comparative evaluation. This is typically the conventional microprocessor control that operates in accordance with a corresponding, novel operating program.

BRIEF DESCRIPTION OF THE DRAWINGS

Advantageous modifications of the invention are or described in detail below in the description of preferred embodiment of the invention, in conjunction with the figures. Shown are in.

DESCRIPTION OF THE PREFERRED EMBODIMENTS

Figure 1:
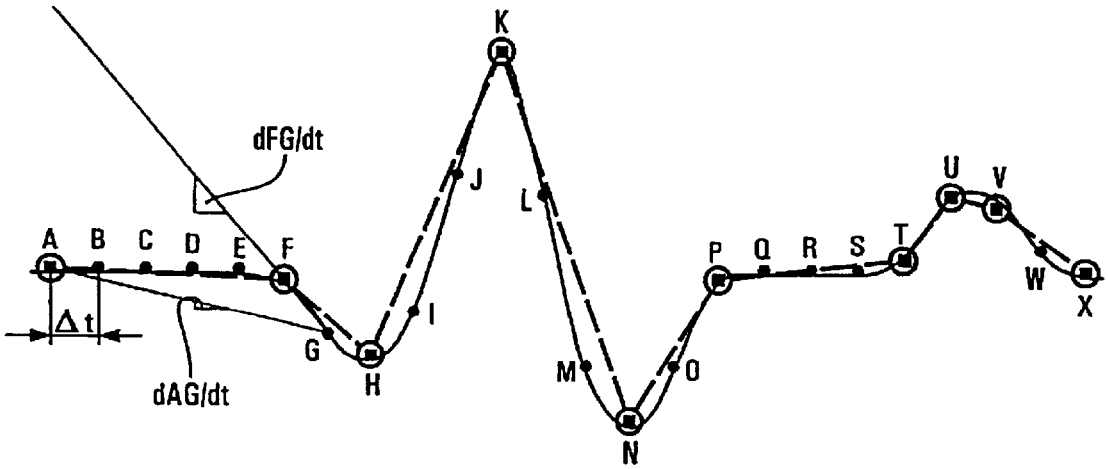
FIG. 1 the schematic, graphic representation of an EKG signal, along with its representation according to the method of the invention, FIG. 2 a flow diagram of the course of the method of the invention in an embodiment, FIG. 3 a schematic representation of the data-word structure in an embodiment of the method, FIG. 4 an example of an encoding table for the signal amplitudes for use in the method of the invention, FIG. 5 a timing diagram for an embodiment of the method of the invention, FIG. 6 a block diagram and signal-course diagram of an embodiment of the apparatus of the invention, FIG. 7 a scheme of the control-signal statuses that specify the internal signals of FIG. 6, and FIG. 8 a greatly-simplified function block diagram of a cardiac stimulator employing an embodiment of the apparatus of the invention.

To clarify the underlying concept of the method of the invention, FIG. 1 shows the simplified, graphic representation of a QRS complex as a part of an EKG signal (solid line) along with its approximation (dashed line), which is obtained through the method. The filled circles and squares characterized by capital letters and appearing over the course represent the signal samples obtained at a constant sampling interval $\Delta t$; the squares characterize the signal samples that are stored or transmitted as a result of the method.

The representation clarifies the principle of the method by way of the example of the signal samples G as a current 20 signal sample as F as a previous signal sample: The increase dFG/dt of the straight connecting line between points F and G is determined and compared to the increase dAG/dt of the straight connecting line between point G and point A, the last-stored signal sample. Because the difference (dFG/dt—dAG/dt) exceeds a predetermined value—not shown in the graph—the signal sample F is now stored as the last value, with the inclusion of the operational sign, amplitude value and numerical value of the sampling intervals that have passed since the last storage (or since a defined time 0).

The signal sample F would now be made the basis of the further comparisons. Since, for example, in the signal samples D and E the same procedure yielded a difference between increase values that was lower than the threshold value, these signal samples were not stored. (The procedure for signal samples A through C is not clarified solely by the illustrated signal section; for more information, refer to signal sections preceding "A" in time, or special starting conditions for the procedure that need not be explained here.)

Figure 2:
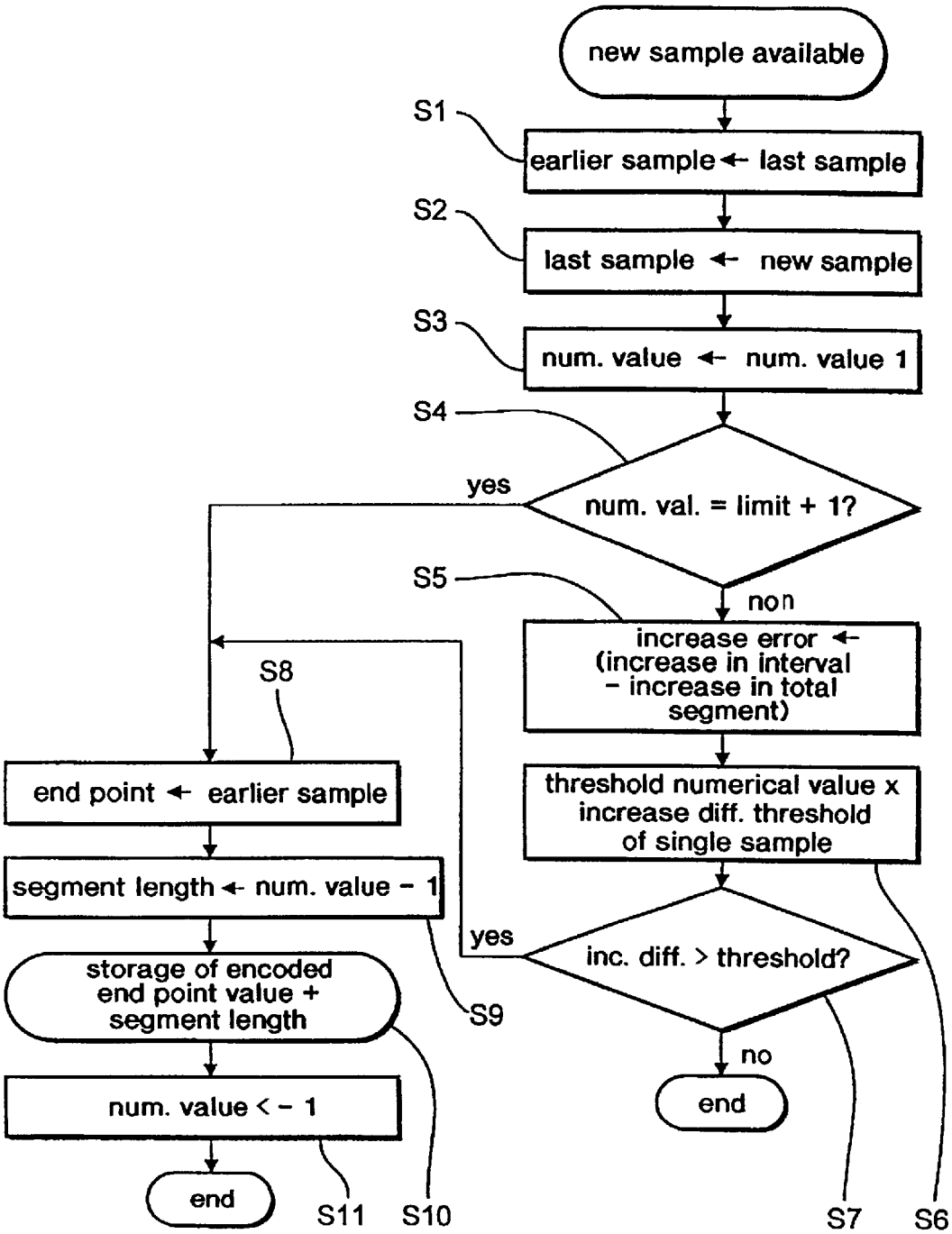

In a flow diagram, FIG. 2 illustrates the course of the method of the invention in an embodiment in which the time at which a (random) new signal sample is present constitutes the starting point:

In a first step S1, the signal sample that is current up to the point at which the new signal sample is ready is redefined as the "earlier sample"; in a step S2, the newly-obtained signal sample is substituted for the first as the "current sample"; in a step S3, the numerical value is incremented by one, and in a step S4, the decision is made as to whether the new numerical value is one above a predetermined limit. The flow diagram branches off here:

If this is not the case ("no"), step S5 is the next step; here, the amount of the difference between the current sample and the last-stored sample is determined from the increase in the last measuring interval and the increase in the total segment, and the difference is defined as the increase difference. In a following step S6, the product is formed from the current numerical value and a threshold value—established for a sampling time interval—of a permissible deviation of the increase-difference values, and defined as a current threshold value, which as explained above, is the basis of a comparison of the increases in the last measuring interval and the total interval up to the last-stored sample. In the following step S7, it is determined whether the increase difference determined in step S5 is greater than the threshold value determined in step S6.

Here the flow diagram branches off again: If the increase difference is not greater than the threshold value ("no"), this ends the sequence of steps of the procedure of deciding whether the current signal sample is to be stored or transmitted, so that no storage or transmission is initiated.

If, however, it is greater ("yes"), the procedure follows the path started in step S4 with the case that the new numerical value is one above the limit ("yes" in step S4). In the first step of this path, S8, the earlier sample is defined as the new end point. In a next step S9, the segment length is defined with the current numerical value decremented by one. In the consecutive step S10, the end point defined in step S8 (to be exact: its operational sign and amplitude value in encoded form—see below) is stored, as is the segment length defined in step S9 and, finally, "1" is used as the new numerical value in step S11, whereupon the program in this path ends.

FIG. 3 gives, in a schematic representation, an example for the data-word structure that is used in a preferred execution of the storage of the signal samples within the scope of the method. As can be seen from the figure, there are data-word fields for the temporal association of the signal sample (signal length—$L_2$ to $L_0$), for the operational sign of the signal amplitude (end-point operational sign s) and the amplitude value (end-point value—$v_3$ to $v_0$). The special structure in the last-mentioned field shown in the figure is suitable for an efficient utilization of the available word width—in this case, 8 bits—for storing small signal amplitudes with high resolution in comparison to large amplitudes. For this purpose the signal amplitude is associated with one of three precision zones through the combination of $v_3$ and $v_0$ (refer to the last column of the table).

With respect to the segment-length field, it is pointed out that an encoded value of "0" stands for a segment length having a value of "8," because a segment length of zero does not occur. In the figure, $V_{max}$ stands for the maximum magnitude of the (digitized) signal-sample amplitude, and results as $V_{max}=2^{(\#bits-1)}$ where "#bits" is the processing width in the A/D conversion. of course, a larger word width—assuming a constant maximum amplitude—permits a higher temporal and/or amplitude resolution for the S and V fields because of the greater available length.

FIG. 4 shows an example for an encoding table for a signal having signal-amplitude values S of 0 to 31 in 6-bit encoding (1 bit for the operational sign, 5 bits for the amplitude value) in encoded amplitude values V. The underlined values indicate the attainment of a new stage in the encoded value. The comparatively higher resolution with low S values is readily apparent.

Figure 5:
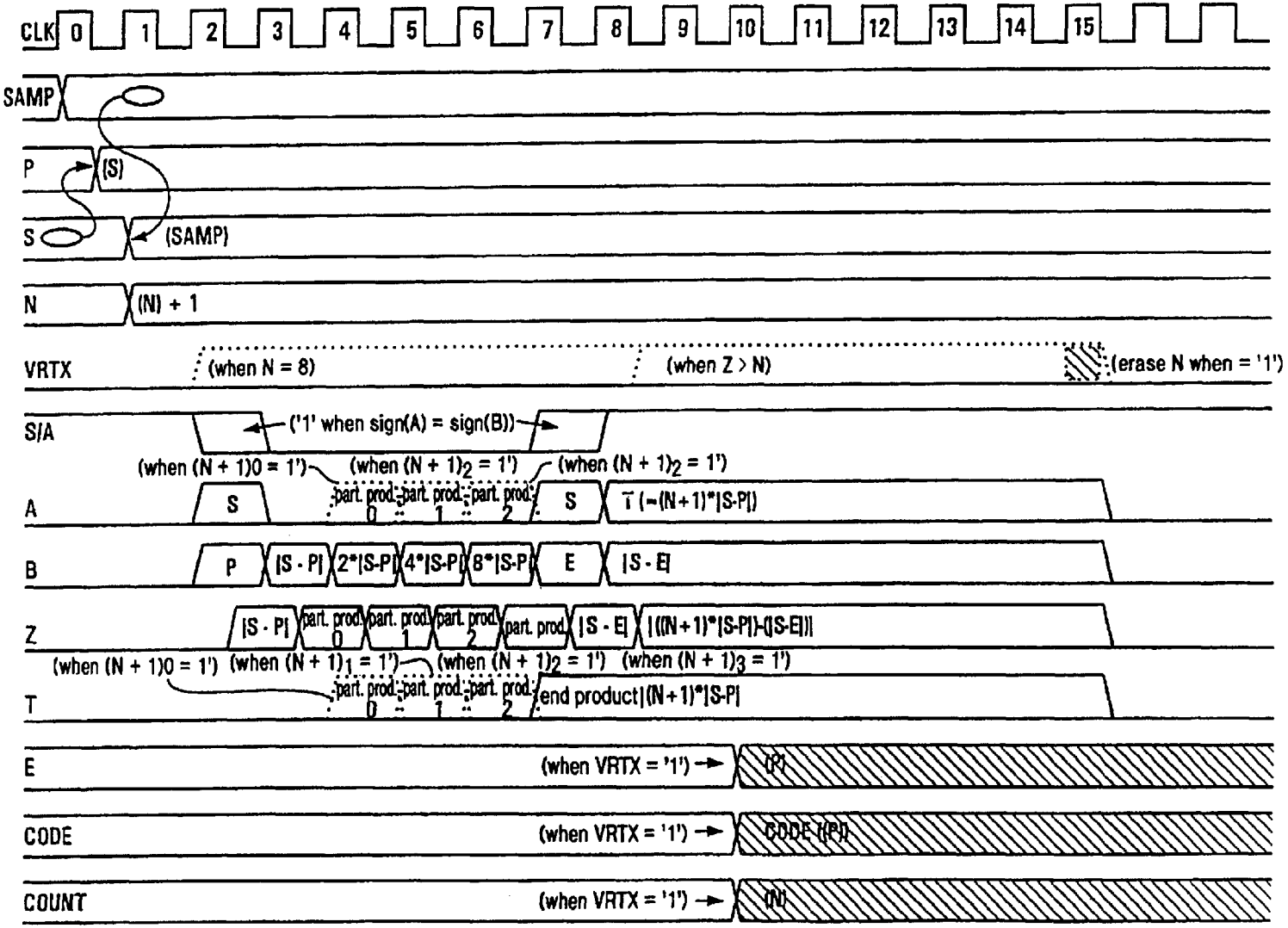

FIG. 5 shows a schematic representation of a timing diagram for an embodiment (corresponding to FIG. 2) of the control process in the method of the invention, using the following abbreviations:

CLK=clock

SAMP=new EKG signal in operational sign/value format

P=earlier signal-sample value

S=current signal-sample value

N=segment-length counter

VRTX=control signal used when the segment end point is required

S/A=ALU operation-type control signal

A=ALU input register

B=ALU input register

Z=ALU output register

T=intermediate-memory register

E=segment end point value

CODE=encoded segment end point

COUNT=segment-length value (The control signal "VRTX" is used if the maximum permissible segment length—also referred to as "limit" in the description of FIG. 2—is attained or the determined change in increase requires the definition of a new end point.)

Figure 6:
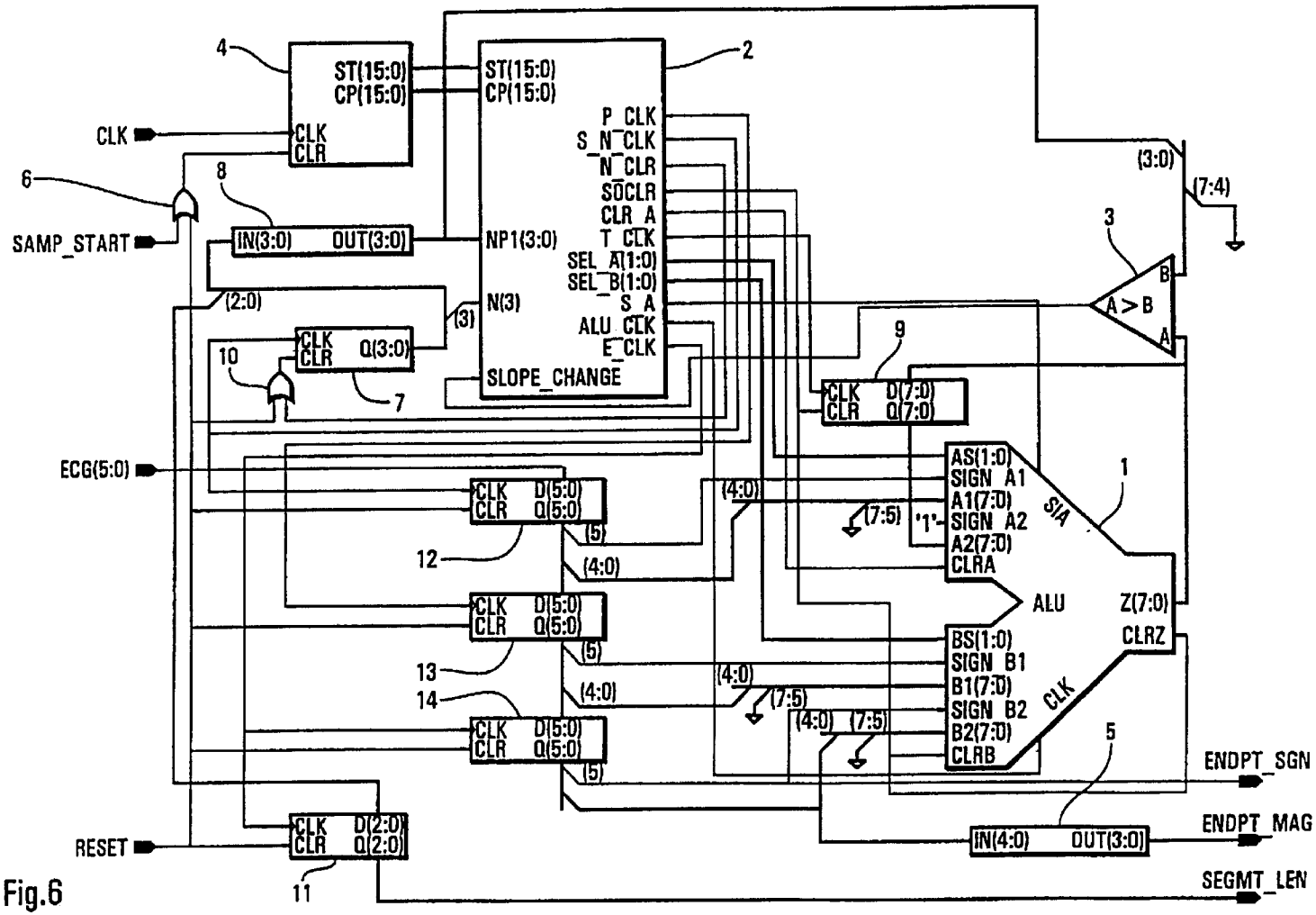

FIG. 6 is a block diagram and signal-path diagram of an embodiment of the apparatus of the invention that implements the course of the method outlined in FIGS. 2 and 5, and FIG. 7 is a scheme of the control-signal statuses that is part of this course.

As shown in the left edge of FIG. 6, the input signals "CLK" (clock signal from a clock generator), "SAMP—START" (start signal, for example of an input stage having and additional control-signal output), "ECG[5:0]" (signal sample from the A/D converter as a 5-bit bus signal) and "RESET" of devices not shown in the figure are supplied to the arrangement. As can be seen at the right edge of the figure, after the formation of a single data word, the arrangement emits the bus data signals "ENDPT—SGN" (operational sign of the signal amplitude), "ENDPT—MAG" ([absolute] value of the signal amplitude) and "SEGMT—LEN" (segment length defining the temporal association of the sample) as a result of processing for the purpose of internal storage or transmission to an external device.

For specifying the internal signals shown in the figure, refer to the status table of FIG. 7; only an abbreviated verbal description of the arrangement and the cooperation of the components and the signal flows is given.

The primary components of the illustrated arrangement are an arithmetic and logic unit (ALU) 1, a control decoder 2, which is linked on the output side to different signal and control inputs of the ALU and clocks their operation, and a comparator 3. A status counter 4, an amplitude-value encoder into 5 and a plurality of logic gates and registers are associated with these components in the manner shown in the figure. The external clock signal is supplied directly to the status counter 4, and the "SAMP—START" signal is supplied to the reset input of the status counter 4 by way of an OR gate 6 provided on the input side of the status counter 4 and to whose second input the "RESET" signal travels.

The status counter 4 is connected on the output side to the control decoder 2. Also connected on the output side to the control decoder are a first segment-length register (counter) 7 and a second segment-length register (incrementer) 8, which is connected in turn on the input side to the counter, and, finally, the signal-increase comparator 3, which is fed by way of its one input with the output signal of the second segment-length register 8 and by way of its second input by the ALU 1 and a T register 9—see below. A second OR gate 10, at whose one input the "RESET" signal is present, and at whose other input a reset signal "N—CLR" generated by the control decoder 2 is present, is connected to the reset input of the first segment-length register. The clock signal "N—P—CLK" generated by the control decoder 2 is present at the clock input of the first segment-length register 7.

The output signal of the first segment-length register or segment-length counter 7 is also supplied to a further (third) segment-length register 11, whose clock input is supplied by the control decoder 2 with the clock signal "E—CLK," while the reset input receives the "RESET" signal and "SEGMT—LEN" is ready at the output as an output signal of the arrangement.

The current signal-sample input signal "ECG[5:0]" is supplied to the signal input of an S register (register for the current signal-sample amplitude value) 12, at whose clock input the clock signal "S—N—CLK" generated by the control decoder 2 is present and at whose reset input "RESET" is present. The output of the S register 12 is connected to the signal input of a P register 13 (register for the earlier signal-sample amplitude value), and it furthermore delivers (separately) an operation-sign output signal and an amplitude-value output signal to the ALU 1. The P register 13 is wired analogously to the S register, and is connected on the output side to a further register, the E register 14 (for the segment end point value), which, again, is wired analogously on the input side, and delivers "ENDPT—SGN" and a (non-encoded) amplitude signal as output signals. The latter is supplied to the input of the ALU 1 and the input of the encoder 5, which in turn delivers the encoded output signal "ENDPT—MAG."

Finally, the T register 9 is provided in the arrangement as an intermediate memory whose signal input is connected to the signal output of the ALU 1, whose operation is again clocked by the control decoder 2 and whose reset input is respectively connected to an erase-signal output of the control decoder 2 and the ALU 1.

The operation of the arrangement results (with consideration of the signal-status table of FIG. 7) form the flow diagram of FIG. 2 and the timing diagram of FIG. 5, and is therefore not explained again here.

The following notes apply for FIG. 7:

? (0) control value='1' exactly when $[N+1]_0$='1' (i.e., LSB of the result of the increment of the numerical value of one)

? (1) control value='1' exactly when $[N+1]_1$='1'

? (2) control value='1' exactly when $[N+1]_2$='1'

? (3) control value='1' exactly when $[N+1]_3$='1'

? (4) control value='1' exactly when [N]=8 (i.e., segment-numerical value maximal)

? (5) control value='1' exactly when [Z]>[N] (i.e., change in increase is greater than 1*LSB per sampling interval)

? (6) control value='1' exactly when VRTX='1.'

The control signals "ALU S—A" and "VRTX" must be placed in intermediate storage ("latched"—in an S-R flip-flop, for example—so that their respective status can remain stable during the status-numerical value changes.

FIG. 6 illustrates an arrangement having one input channel, but that can be expanded to two or more channels, in which case a synchronization of the data flows may be provided such that, each time the change in increase of the signal in one of the channels necessitates the definition of a new end point, one is simultaneously defined in the other channels as well.

Figure 8:
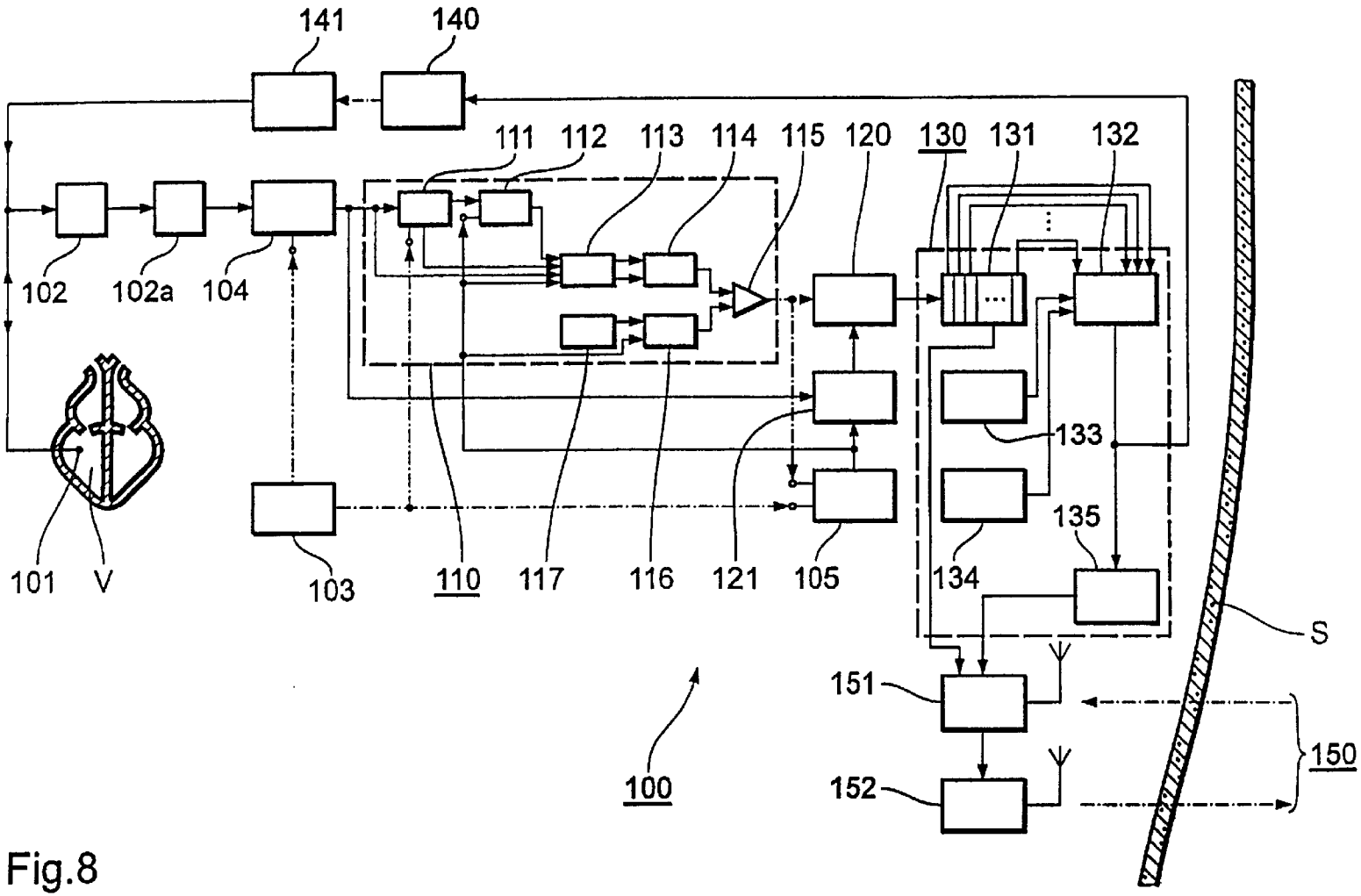

FIG. 8 shows a greatly-simplified function block diagram of a cardiac stimulator 100 employing an embodiment of the apparatus of the invention. (Refer to FIGS. 6 and 7 with respect to the concrete implementation of the latter.)

An electrode 101 serving to receive cardiac-action potentials and supply stimulation pulses to the heart tissue is disposed in the ventricle V of the heart of a patient. This electrode is connected in a standard manner to sensing amplifier 102 for amplifying and conditioning the cardiac signals. An A/D converter 102a for digitizing the amplitude values is disposed downstream of the sensing amplifier 102. A clock generator 103 controls the operation of a sample & hold circuit 104 disposed downstream of the A/D converter 102a such that the amplifier value of the recorded cardiac signal is registered in time intervals predetermined by the clock frequency, and held until the next clock pulse. Moreover, the clock generator is connected to the input of a counter 105 as well as a control input of a signal-compression calculating unit 110.

The calculating unit 110 includes as function units a first intermediate memory 111 for the second-to-last-registered (in the sense of FIG. 3, the "earlier") signal sample, into which memory the signal value (including operational sign) previously held in the sample & hold circuit 104 is reloaded at the clock signal of the clock generator 103. Moreover, the calculating unit includes a second intermediate memory 112, in which the signal sample (in the segment length; operational sign; signal value format) used last in the course of the signal compression is stored. The two memories and the output of the sample & hold circuit 104 and the counter 105 are connected to data inputs of an arithmetic stage 113, which performs the calculation of the current signal increase and the increase for the last stored signal sample described in detail above. The increase values are ready on the output side of the arithmetic stage 113, and are supplied to the inputs of a subtraction stage 114 that determines the difference in increases.

The output of the subtraction stage is connected to an input of a comparator 115, whose other input is connected to the output of a multiplication stage 116. This stage is again connected on the input side to a threshold-value memory 117, in which a pre-programmed increase threshold value (for a segment length 1) is stored, and to the output of the counter 104, and calculates the increase threshold value related to the current segment length, with which the established increase difference is to be compared. As a result of the comparison, the comparator 115 (and thus the calculating unit 110) emits a control signal.

This control signal is supplied, on the one hand, to a reset input of the counter 104, and always resets it if the comparison has revealed that the increase difference is greater than the current threshold value. On the other hand, the signal is supplied to the input of a memory-control unit 120, whose switching signal effects the enabling of the data input of a signal-form memory 131, in each of whose memory regions a compromised signal form is stored.

The data words supplied to this input have the format (segment length; operational sign; amplitude value), and are generated in an encoder 121 from the current output values of the sample & hold circuit 104 and the counter 105 in that an amplitude encoding is simultaneously performed with an association table in the manner shown in FIG. 4. (As an alternative, the digitized signal values obtained at the output of the A/D converter 102a can flow directly into the data words.)

The signal-form memory 131, whose regions can be accessed separately and optionally, is connected to data inputs of a signal-form evaluation unit 132. Corresponding to programs stored in an operation-program memory 133, this unit checks each currently-determined total-signal course of an intracardially-recorded EKG for the presence of predetermined signal-form criteria (likewise stored in the memory 131 or in a separate data memory 134), and/or, using significance criteria stored in the memory 134, for the presence of significant deviations form EKGs detected earlier.

Diagnostic criteria whose processing with the signal-form comparison data in a hierarchically-superordinate, second processing plane in the evaluation stage 132 makes it possible to autonomously obtain data in the apparatus that directly represent diagnostic information are simultaneously stored in the memory 134. On the one hand, these data are stored in a diagnosis memory 135 and, on the other hand, they are supplied to the input of a stimulation-control unit 140 that is know per se and obtains from the data the control signals for a pulse generator 141 for demand-wise stimulation of the ventricle by way of the electrode 101, and correspondingly actuates the pulse-generator—for example, in the case that an occurrence of ventricular tachycardia is determined using the signal-form comparison, such that a pulse sequence that terminates the tachycardia is emitted.

The data stored in both the signal-form memory 120 and the diagnosis memory 131 are ready for external request, by way of a telemetry segment 150, for transmission through the skin S to the outside of the patient. The (serial) transmission of the data to a transmitting unit 152 is enabled and controlled after reception of a corresponding request signal through a telemetry control unit 151. In accordance with the above description, the apparatus 100 is to respond as a self-sufficient, integrated diagnosis and therapy device, and is also selectively in connection with a physician periodically monitoring the diagnosis results. Moreover, means for internal, possibly also time-related, registration of stimulation or other operating parameters can be provided in a manner know per se, so that a retrospective operation check of the device becomes possible at the same time.

The invention is not limited in its implementation to the preferred embodiment disclosed above. Rather, a plurality of variations that makes use of the illustrated solution, even in fundamentally different embodiments, is conceivable.

We claim:

1. Method of storing signals having a course over time in an implantable medical device and/or transmitting the signals out of the device and out of a patient's body, said method comprising the steps of:

sensing physiological signals of a patient's body;

detecting a course over time associated with said sensed physiological signals in the device, said course over time being detected at predetermined time intervals with a constant sampling interval;

obtaining a quantity of signal samples from the detected course over time;

selecting a partial quantity of said obtained signal samples based on predetermining selection criterion wherein the selection criterion is the first derivation of the course over time of the signals according to time and said selecting step includes determining an initial first derivation of the straight-line connection between an nth and the (n−1)th signal sample; and comparing the initial first derivation to an earlier first derivation of the straight-line connection between [(n−1)th] *nth* signal sample and the last-stored and/or last-transmitted signal sample; and storing and/or transmitting the [nth] *(n−1)th* signal sample as the new last signal when the initial first derivation and the earlier first derivation differ by more than a predetermined value.

2. Method according to claim 1, wherein the storing and/or transmitting step further includes storing or transmitting, for each stored and/or transmitted signal sample, the operational sign, the amplitude value and the duration of the time intervals that have passed since the last storage of a signal sample are stored or transmitted in a single data word.

3. Method according to claim 1, further comprising the step of holding the last-transmitted signal sample in intermediate storage in the case of time-near transmission of the signal samples of the partial sequence.

4. Method according to claim 1, wherein the step of obtaining signal samples comprises digitizing amplitude values.

5. Method according to claim 4, wherein the digitizing of smaller amplitude values is effected with a higher resolution than that of large amplitude values.

6. Method according to claim 1, wherein the physiological signals are cardiac-action signals, and further comprising the step of transmitting an intracardially-recorded EKG, or model or comparison signals representative thereof from outside of the patient's body.

7. Apparatus for storing signals having a course over time in an implantable device, said apparatus comprising:

a timer for establishing sampling intervals, a signal recorder for recording the signal-amplitude value in the sampling intervals, a processing unit that is connected to the timer and at least indirectly to the signal recorder for processing the recorded signal-amplitude values corresponding to a predetermined algorithm, and for outputting a memory-control signal as a result of the processing, a counter that is connected to the output of the timer and, by way of a reset input, to the control-signal output of the processing unit for counting the sampling intervals in response to the memory-control signal, and for outputting an interval-counter value that is also supplied to the processing unit, a memory that can be at least indirectly connected to the output of the signal recorder and the output of the counter for storing signal samples from the counter status, signal operational sign and signal amplitude as data words, and a memory-control unit that is connected to the control-signal output of the processing unit for producing a connection between the output of the signal recorder and the output of the counter and the memory in response to the memory-control signal, and for effecting storage of the current signal sample, said processing unit having:

a first and a second intermediate-storage unit for intermediate storage of the signal sample that was last stored in the memory, and the second-to-last-recorded signal sample, an arithmetic stage that is at least indirectly connected to the outputs of the signal recorder and the counter, and the first and second intermediate-storage units, for calculating the first derivations of the straight-line connection between the current and second-to-last signal samples and the straight-line connection between the [second-to-last-] *current* and the last-stored signal samples, a subtraction stage that is connected to the arithmetic stage for forming the difference from the first derivations, a threshold-value memory for storing a difference threshold value, and a comparator unit that is connected on the input side to the subtraction stage and the threshold-value memory for comparing the difference of the first derivations to the difference threshold value, and for outputting the memory-control signal as a result of the comparison.

8. Apparatus according to claim 7, wherein the memory is configured as a semiconductor direct-access memory, and has a plurality of separately-accessible memory regions for respectively storing a signal-sample partial sequence.

9. Apparatus according to claim 7, wherein the signal recorder has at least one electrode, which has a downstream sensing amplifier, for detecting cardiac-action potentials.

10. Apparatus according to claim 7, wherein the implantable device is an implantable anti-arrhythmia device for treating arrhythmias of the heart, particularly a defibrillator and/or cardiac pacemaker or a medication-dosing device.

11. Apparatus according to claim 7, further comprising a transmitting unit, the transmitting unit being connectable to the memory for transmitting memory contents out of the device, and means are provided for activating the transmitting unit on demand or in predetermined time intervals.

12. Apparatus according to claim 7, further comprising a control- or diagnosis-data calculating unit that is connected on the input side to the memory for the signal-sample partial sequences and, on the output side, selectively to a control- or diagnosis-data memory, and said calculating unit is configured for comparative processing of different stored signal samples for obtaining control signals or diagnostically-relevant data.

13. Apparatus for storing signals having a course over time in an implantable device and/or transmitting the signals out of the device and out of a patient's body, said apparatus comprising:

a timer for establishing sampling intervals, a signal recorder for recording the signal-amplitude value in the sampling intervals, a processing unit that is connected to the timer and at least indirectly to the signal recorder for processing the recorded signal-amplitude values corresponding to a predetermined algorithm, and for outputting a memory-control signal as a result of the processing, a counter that is connected to the output of the timer and, by way of a reset input, to the control-signal output of the processing unit for counting the sampling intervals in response to the transmission-control signal, and for outputting an interval-counter value that is also supplied to the processing unit, a transmitter that can be at least indirectly connected to the output of the signal recorder and the output of the counter for transmitting signal samples from the counter status, signal operational sign and signal amplitude as data words out of the apparatus, and a transmission-control unit that is connected to the control-signal output of the processing unit for producing a connection between the output of the signal recorder and the output of the counter and the transmitter in response to the transmission-control signal and for effecting a transmission of the current signal sample, said processing unit having:

a first and a second intermediate-storage unit for intermediate storage of the signal sample that was last stored in the memory, and the second-to-last-recorded signal sample, an arithmetic stage that is at least indirectly connected to the outputs of the signal recorder and the counter, and the first and second intermediate-storage units, for calculating the first derivations of the straight-line connection between the current and second-to-last signal samples and the straight-line connection between the [second-to-last-] *current* and the last-stored signal samples, a subtraction stage that is connected to the arithmetic stage for forming the difference from the first derivations, a threshold-value memory for storing a difference threshold value, and a comparator unit that is connected on the input side to the subtraction stage and the threshold-value memory for comparing the difference of the first derivations to the difference threshold value and for outputting the memory-control signal as a result of the comparison.

14. Apparatus according to claim 13, wherein the transmitting unit is configured as a telemetry transmitting unit.

15. Implantable anti-arrhythmia device comprising:

a timer for establishing sampling intervals, a signal recorder for recording the signal-amplitude value in the sampling intervals, a processing unit that is connected to the timer and at least indirectly to the signal recorder for processing the recorded signal-amplitude values corresponding to a predetermined algorithm, and for outputting a memory-control signal as a result of the processing, a counter that is connected to the output of the timer and, by way of a reset input, to the control-signal output of the processing unit for counting the sampling intervals in response to the transmission-control signal, and for outputting an interval-counter value that is also supplied to the processing unit, a transmitter that can be at least indirectly connected to the output of the signal recorder and the output of the counter for transmitting signal samples from the counter stains, signal operational sign and signal amplitude as data words out of the apparatus, and a transmission-control unit that is connected to the control-signal output of the processing unit for producing a connection between the output of the signal recorder and the output of the counter and the transmitter in response to the transmission-control signal and for effecting a transmission of the current signal sample, said processing unit having:

a first and a second intermediate-storage unit for intermediate storage of the signal sample that was last stored in the memory, and the second-to-last-recorded signal sample, an arithmetic stage that is at least indirectly connected to the outputs of the signal recorder and the counter, and the first and second intermediate-storage units, for calculating the first derivations of the straight-line connection between the current and second-to-last signal samples and the straight-line connection between the second-to-last- and the last-stored signal samples, a subtraction stage that is connected to the arithmetic stage for forming the difference from the first derivations, a threshold-value memory for storing a difference threshold value, and a comparator unit that is connected on the input side to the subtraction stage and the threshold-value memory for comparing the difference of the first derivations to the difference threshold value and for outputting the memory-control signal as a result of the comparison, and further comprising an operation control unit that is connected on the input side to the output of the control-data calculating unit and/or the control-data memory, said operation-control unit is configured to control the operation of the anti-arrhythmia device based on the result of the comparative evaluation.

* * * * *